United States Patent [19]

Ector, Jr.

[11] Patent Number: 4,658,816

[45] Date of Patent: Apr. 21, 1987

[54] LIGHTED CANALICULUS INTUBATION SETS

[75] Inventor: W. Lane Ector, Jr., Clearwater, Fla.

[73] Assignee: Concept Incorporated, Clearwater, Fla.

[21] Appl. No.: 671,413

[22] Filed: Nov. 14, 1984

[51] Int. Cl.[4] .................................................. A61B 17/36
[52] U.S. Cl. .................................. 128/303.1; 128/397; 604/8; 604/264
[58] Field of Search .................. 604/21, 8, 264, 280, 604/283, 284; 128/303.1, 303.11, 395, 397

[56] References Cited

U.S. PATENT DOCUMENTS

| | | | |
|---|---|---|---|
| 2,154,968 | 4/1939 | Alkio | 604/264 |
| 3,089,484 | 5/1963 | Hett | |
| 3,146,775 | 9/1964 | Moore et al. | |
| 3,261,356 | 7/1966 | Wallace | 604/264 |
| 3,278,739 | 10/1966 | Royka et al. | |
| 3,285,242 | 11/1966 | Wallace | |
| 3,360,640 | 12/1967 | Seitz et al. | |
| 3,431,410 | 3/1969 | Dolan et al. | |
| 3,528,720 | 9/1970 | Treace | |
| 3,630,198 | 12/1971 | Henkin | 604/280 |
| 3,726,284 | 4/1973 | Parker | 604/8 |
| 3,794,091 | 2/1974 | Ersek et al. | |
| 3,809,072 | 5/1974 | Ersek et al. | 128/397 |
| 3,858,586 | 1/1975 | Lessen | 128/303.1 |
| 3,948,272 | 4/1976 | Guibor | 604/264 |
| 4,236,520 | 12/1980 | Anderson | 604/264 |
| 4,269,192 | 5/1981 | Matsno | 604/264 |
| 4,273,109 | 6/1981 | Enderby | 128/303.1 |
| 4,305,395 | 12/1981 | Martinez | 604/54 |
| 4,311,138 | 1/1982 | Sugarman | 604/21 |
| 4,380,239 | 4/1983 | Crawford et al. | |

FOREIGN PATENT DOCUMENTS 456061  3/1950  Italy .................................. 604/264

OTHER PUBLICATIONS

U.S. Application Ser. No. 65,222 filed Aug. 19, 1970, cited in U.S. Pat. No. 3,809,072.

Primary Examiner—C. Fred Rosenbaum
Assistant Examiner—Gene B. Kartchner
Attorney, Agent, or Firm—Frijouf, Rust and Pyle

[57] ABSTRACT

An intubation device is disclosed for use with a light source for the reconstruction of the lacrimal ducts of a patient. The device comprises a first and a second base each being suitable for attachment to the light source. A first and second probe each having a proximal end and a distal end comprise light conducting means to permit the transmission of light along the interior length of the probes between the proximal ends and the distal ends. The proximal ends of the first and second probes are respectively connected to the first and second bases to permit entry of light from the light source to the proximal ends of the first and second probes. A flexible translucent tubing means having a first and a second sheath portions and an intermediate portion enables the first and second sheath portions to removably encompass the first and second probes. The first and second probes and sheath portions are insertable into the lacrimal ducts of the patient with the distal ends of the first and second sheath portions being luminating by the light source to aid in the location thereof in the nasal cavity of the patient. The first and second sheaths are removable from the probes enabling the distal ends of the sheath portions to be pulled from the nasal cavity to position the intermediate portion into the lacrimal duct of the patient.

19 Claims, 15 Drawing Figures

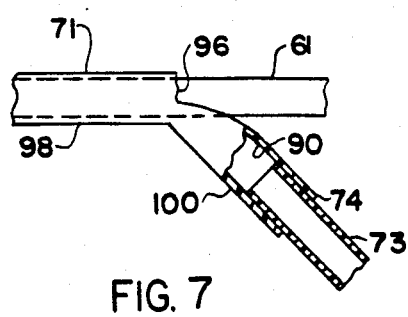
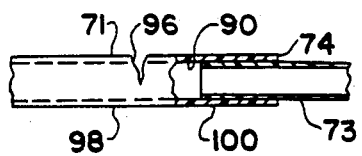
FIG. 7    FIG. 8
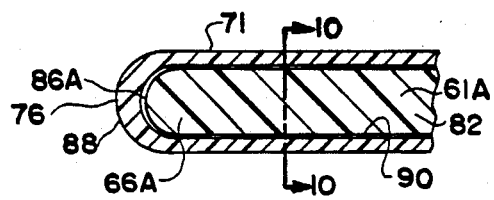
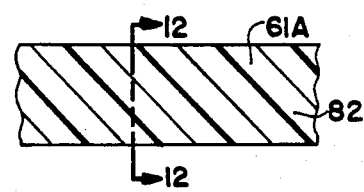
FIG. 9    FIG. 11
FIG. 10    FIG. 12
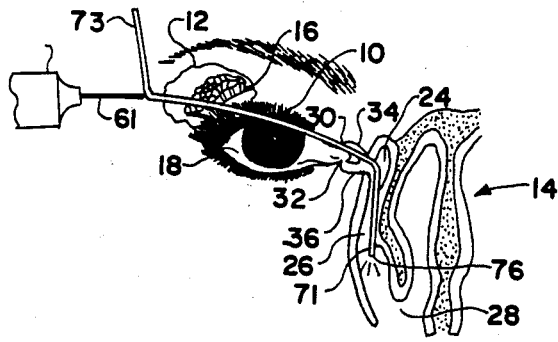
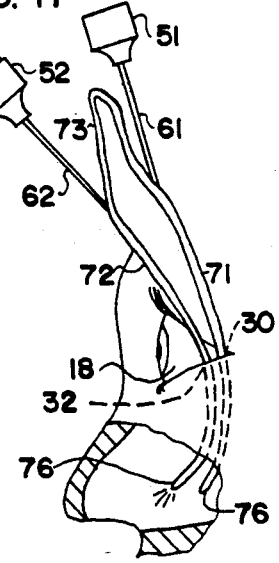
FIG. 13    FIG. 14
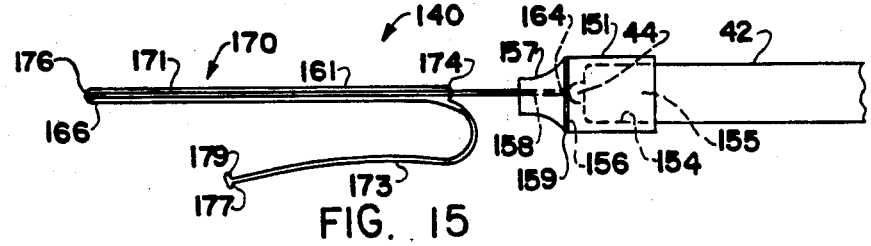
FIG. 15

LIGHTED CANALICULUS INTUBATION SETS

BACKGROUND OF THE INVENTION

1. Field of the Invention

This invention relates to medicine and surgery and more particularly in an intubation device for positioning a probe or intubator into a duct of a patient.

2. Description of the Prior Art

It is well known in the medical art that lacrimal fluids or tears are continuously supplied from lacrimal glands to wash across the sclera and cornea of the eye. Any excessive lacrimal fluid is drained by a duct system known as lacrimal ducts to the nasal passage to maintain an appropriate amount of fluid for retention by the eye.

Some patients experience a partial or permanent closure in the canaliculi, the lacrimal sac or the nasolacrimal duct thus blocking the drainage of lacrimal fluid into the nasal cavity. As a result of this blockage, the eye will continue to tear as the only means of dissipating the continuous flow of lacrimal fluid onto the cornea of the eye. The continuous tearing of the eye not only causes much discomfort and annoyance for the patient but also may result in more serious diseases of the eye if the condition is not corrected.

Various solutions have been proposed by the prior art to reopen the lacrimal drainage ducts of a patient. U.S. Pat. No. 2,154,968 to Alkio discloses a method and apparatus for enlarging the lacrimal ducts through the insertion of a tube in order to preliminarily enlarge the duct. Thereafter, a spiral cannula is inserted into the duct through the nose and is then drawn upwardly into the duct. The tube is then removed leaving the cannula in the duct for drainage of secretion between the spirals of the cannula.

U.S. Pat. No. 3,726,284 to Parker discloses a replacement tube for the lacrimal drainage ducts having a tube comprising elongated end portions with an expanded central portion which adjoins the adjacent end portions. The end portions exhibit a drainage passage extending therethrough and communicating with the expanded central portion.

U.S. Pat. No. 3,948,272 to Guibor teaches a reconstructive replacement channel for a lacrimal drainage duct including a pair of steel probes surrounded by a silicon tubing which is inserted inwardly into the lacrimal duct. The probe has a helix shape to enable the probe to be inserted with greater ease into the lacrimal passage.

U.S. Pat. No. 4,305,395 to Martinez discloses an intubation set having a first and a second probe, each having a flexible sheath thereon interconnected by an intermediate tubing. The pair of probes are passed through the puncti lacrimalia, the canaliculi, the lacrimal sac and the nasolacrimal ducts into the nose. The probes were then withdrawn leaving the flexible sheaths. The sheaths were then pulled from the nose to position the intermediate tubing into the lacrimal ducts.

The foregoing patents have met with varying success in solving the needs of the medical art. For example, the invention disclosed in U.S. Pat. No. 4,305,395 has solved many of the important needs in the medical art and in many instances was the optimum solution for patients suffering from the foregoing illnesses. However, on occasion, the physician experienced difficulty in locating the distal ends of the probes when the probes were positioned in the nasal cavity of the patient.

Accordingly, it is a primary object of this invention to improve upon the foregoing patents and provide an intubation device for insertion within a duct of a patient wherein the distal ends of the probes may be conveniently and quickly located by the physician by illuminating the distal ends of the probes with a light source.

Another object of this invention is to provide an intubation device which may be readily and economically affixable to a portable light source or flashlight which light sources are generally available in the medical art.

Another object of this invention is to provide an intubation device for use with a light source having a first and a second probe encompassed by a first and a second translucent sheath with the probes being affixable to the light source permitting the sheaths to be inserted within the ducts of a patient with distal ends of the sheaths being illuminated by the light source.

Another object of this invention is to provide an intubation device for use with a light source wherein the first and second probes comprise light conducting means to permit the transmission of light along the interior length of the probes.

Another object of this invention is to provide an intubation device for use with a light source wherein the light conducting means of the first and second probes comprise fiber optic means.

Another object of this invention is to provide an intubation device for use with a light source wherein the first and second sheaths are interconnected by an intermediate portion which may be drawn into the duct of a patient upon the first and second sheaths being drawn through the duct to position the intermediate portion therein.

Another object of this invention is to provide an intubation device for use with a light source wherein the intubation device has a low cost to enable the first and second probes to be disposable after insertion of the first and second sheaths within the ducts of the patient.

Another object of this invention is to provide an intubation device for use with a light source wherein the first and second sheaths of the flexible translucent tubing is less supple than the intermediate portion for maintaining the position of the first and second sheaths on the first and second probes during insertion thereof and for permitting the positioning of the more supple intermediate portion within the duct of the patient.

The foregoing has outlined some of the more pertinent objects of the present invention. These objects should be construed to be merely illustrative of some of the more prominent features and applications of the invention. Many other beneficial results can be attained by applying the disclosed invention in a different manner or modifying the invention within the scope of the invention. Accordingly, other objects and a fuller understanding of the invention may be had by referring to the summary of the invention and the detailed description describing the preferred embodiment in addition to the scope of the invention defined by the claims taken in conjunction with the accompanying drawings.

SUMMARY OF THE INVENTION

The invention is defined by the appended claims with a specific embodiment shown in the attached drawings. For the purpose of summarizing the invention, the invention may be incorporated into an intubation device for use with a light source for intubating a duct of a patient comprising base means being suitable for attachment to the light source. Probe means having a proximal end and a distal end is connected to the base means at the proximal end of the probe means. The probe means has light conducting means to permit the transmission of light along the interior length of the probe means between the proximal end and the distal end. A flexible translucent means includes a sheath portion means having a proximal end and a closed distal end. The sheath portion means removably encompasses the probe means with the distal end of the sheath portion means being adjacent the distal end of the probe means. The probe means and the sheath portion means are insertable into the duct of the patient with the distal end of the sheath portion means being illuminated by the light source to aid in the location of the distal end of the sheath portion means enabling the flexible translucent means to be positioned into the duct of a patient.

In a more specific embodiment of the invention, the invention relates to an intubating device for use with a light source for the reconstruction of the lacrimal duct of a patient. The base means comprises a first and second base means each being suitable for attachment to the light source. A first and a second probe each have a proximal end and a distal end with the proximal ends thereof connected to the first and second base means, respectively. Each of the probes have light conducting means to permit the transmission of light along the interior of said probes between the proximal ends and the distal ends. A flexible translucent tubing means includes a first and a second sheath portion and an intermediate portion. Each of the sheath portions have a proximal end and a closed distal end with the intermediate portion interconnecting the first and the second sheath portions. The first and second sheath portions removably encompass the first and the second probes with the distal ends of the sheath portions being adjacent the distal ends of the probes respectively. The first and second probes and the first and second sheath portions are insertable into the lacrimal ducts of the patient with the distal ends of the first and second sheath portions being illuminated by the light source to aid in the location of each of the distal ends of in the nasal cavity of the patient. The first and second probes are removable from the first and second sheath portions disposed in the lacrimal ducts enabling the distal end of the first and second sheath portions to be pulled into the nasal cavity of the patient to position the intermediate portion into the lacrimal ducts.

Preferably, each of the first and second base means comprise a cylindrical portion for removably receiving at least a portion of the light source within one end of the cylindrical portion. A base end wall is disposed in each of the base means adjacent the other end of the cylindrical portion with the end walls each having an end wall aperture for receiving the proximal end of the probe therein. The first and second base means may be formed of a semi-ridged material for frictional engagement with the light source.

The light conducting means of the present invention preferably utilizes fiber optic means. In one embodiment of the invention, each of the first and second probes includes a metallic tubing having a hollow interior with light conducting means comprising fiber optic means disposed within the hollow interior of each of the first and second probes. In an alternate embodiment of the invention, each of the first and second probes comprises a unitary fiber optic means for receiving the sheath portions thereon.

The intermediate portion in the preferred form of the invention is more supple than the first and second sheath portions enabling the sheath portions to maintain the position of the first and second sheath portions on the first and second probes and for allowing the more supple intermediate portion to be pulled into the lacrimal duct of the patient to provide the necessary treatment of the intubation device.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 7 is a magnified view of a portion of FIG. 2;

FIG. 8 is a view similar to FIG. 7 with a region of a sheath being disposed in a second position;

FIG. 9 is a sectional view similar to FIG. 3 showing an alternate embodiment of the present invention;

FIG. 10 is a sectional view taken along line 10—10 in FIG. 9;

FIG. 11 is a sectional view similar to FIG. 5 of the alternate embodiment of FIG. 9;

FIG. 12 is a sectional view taken along line 12—12 in FIG. 11;

FIG. 13 is a front view illustrating the insertion of a first intubation probe through the superior canal;

FIG. 14 is a side view illustrating the insertion of a second intubation probe through the inferior canal; and FIG. 15 is a side view of a third embodiment of the intubation device of the present invention.

Similar reference characters refer to similar parts through the several views of the drawings.

DETAILED DESCRIPTION OF THE DRAWINGS

Figure 1:
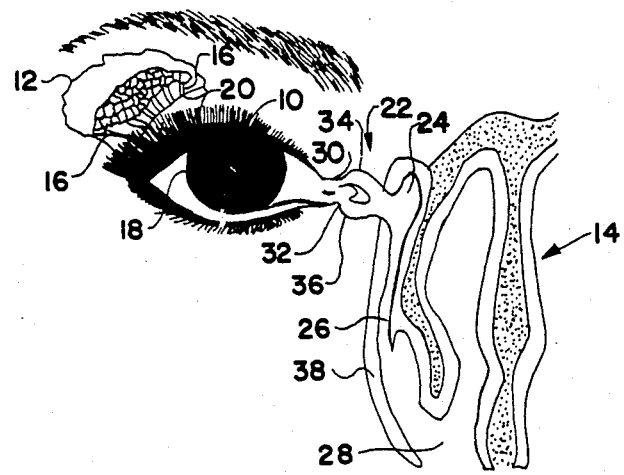
FIG. 1 is a front view partially in section of the lacrimal duct system of a patient.

FIG. 1 is a front view partially in section of a patient showing an eye 10, the lacrimal gland 12 and the nasal cavity shown generally as 14. The lacrimal gland 12 secrets tears through excretory ducts 16 which convey the fluid from the lacrimal gland to the surface or cornea 18 of the eye 10. The excretory ducts 16 open into a series of minute orifices on the upper and outer half of the conjunctiva 20 and are arranged in rows as to disperse the discretion over the surface of the cornea 18.

The lacrimal fluid is carried away by lacrimal canals or canaliculi shown generally as 22 into the lacrimal sac 24 and along the nasolacrimal or nasal duct 26 into the nose cavity 28. The lacimal canals 22 commence at minute orifices known as puncta lacrimalia 30 and 32 and are located on the margins of the lids of the eye remote from the lacrimal gland 12. The superior canal 34 which is smaller and shorter than the inferior canal 36 ascends from the eye and bends at an acute angle to pass inwardly and downwardly into the lacrimal sac 24. The inferior canal 36 descends and then extends horizontally into the lacrimal sac 24. The superior canal 34 and the inferior canal 36 are elastic in structure and permit the entry of probes of the present invention which will be described hereinafter.

The lacrimal sac 24 is the upper dilated extremity of the nasal duct 26. The nasal lacrimal duct 26 sometimes referred to as the nasal duct is a membraneous canal about ¾ of an inch in length which extends from the lacrimal sac 24 to the nose cavity 28 and includes a valve 38 for controlling the flow of lacrimal fluid.

Occasionally, the canaliculi may be obstructed caused by a congenital defect or by some foreign body such as an eyelash or a dacryolith thereby inhibiting the drainage of lacrimal fluids generated by the lacrimal gland 12. In such an event, the lacrimal fluid in the form of tears will run over the lower eyelid. Various other diseases and injuries may result in the obstruction of the canaliculi as well as the lacrimal sac or the nasal lacrimal duct.

Figure 2:
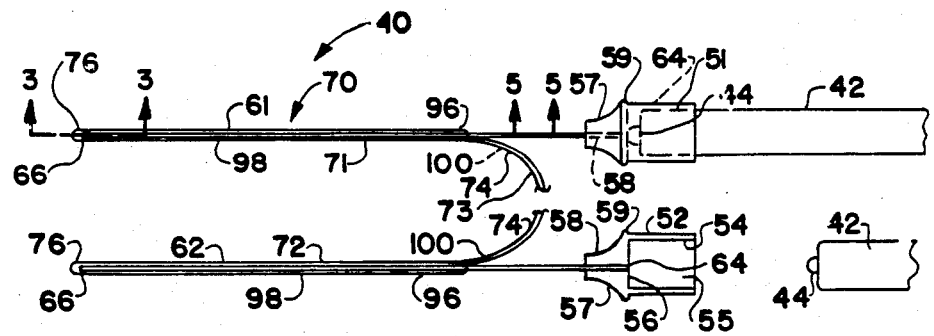
FIG. 2 is a side view partially in section of the intubation device of the present invention.
Figure 3:
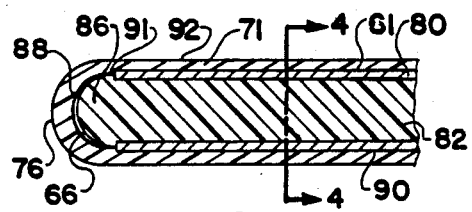
FIG. 3 is an enlarged sectional view taken along line 3—3 of FIG. 2.
Figure 5:
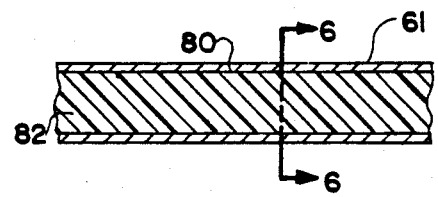
FIG. 5 is an enlarged sectional view taken along line 5—5 of FIG. 2.
Figure 4:
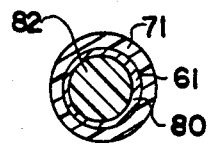
FIG. 4 is a sectional view taken along line 4—4 of FIG. 3.
Figure 6:
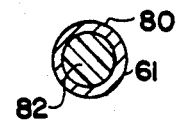
FIG. 6 is a sectional view taken along line 6—6 of FIG. 5.

The present invention contemplates an intubator device for re-establishing the flow of lacrimal fluids into the nose cavity 28. The invention shown in FIG. 2 illustrates an intubator device 40 for use with a light source 42 having a bulb 44. Preferably, the light source is in the form of a cylindrical flashlight as disclosed in U.S. Pat. No. 3,806,724 but it should be understood that various other light sources may be incorporated with the present invention. The intubation device 40 includes base means shown as a first and a second base means 51 and 52 each being suitable for attachment to the light source 42. Each of the base means 51 and 52 preferably comprise a cylindrical portion 54 for removably receiving at least a portion of the light source within an end portion 55. An end wall 56 supports an end boss 57 having an end wall aperture 58. A rim 59 is disposed on the outer periphery of each of the base means 51 and 52 for facilitating removal of the base means from the light source 42. It should be appreciated that the first and second base means 51 and 52 are identical. The light source 42 is shown in the operative position with the first base 51 and is shown in an inoperative position with the second base 52. Since the intubating device are installed sequentially, only a single light source 42 is required for the present invention. Preferably, the first and second bases are made of a semi-ridged plastic material for frictional engagement with the light source as shown with first base 51.

A first and a second probe 61 and 62 which are identical to one another, each have a proximal end 64 and a distal end 66 with the proximal ends 64 being received in the end wall apertures 58 to permit the entry of light from the bulb 44 into the proximal ends 64 of the first and second probes 61 and 62. Each of the probes 61 and 62 have light conducting means to permit the transmission of light along the interior length of the probes between the proximal ends 64 and the distal ends 66. The specific explanation of the light conducting means will be discussed in greater detail with reference to FIGS. 3-6.

A flexible translucent tubing means shown generally as 70, includes a first and a second sheath portion 71 and 72 and in intermediate portion 73. The sheath portions 71 and 72 each have a proximal end 74 and a closed distal end 76 shown in greater detail in FIG. 3. The intermediate portion 73 interconnects the first and second sheath portions 71 and 72 as shown in FIG. 2. The first and second sheath portions 71 and 72 removably encompass the first and second probes 61 and 62, respectively, with the distal ends 76 of the sheath portions 71 and 72 being adjacent the distal ends 66 of the first and second probes 61 and 62.

FIGS. 3-6 illustrate various sectional views of a first embodiment of the first and second probes 61 and 62. The first probe 61 comprises a hollow metallic tubing 80 having a light conducting means 82 which is fiber optic means. The fiber optic means 82 is shown terminating in a hemispherical distal end 86 which is receivable in a hemispherical inner portion 88 of the first sheath portion 71. The distal end 76 of the first sheath portion 71 is also shown terminating in a hemispherical surface. Preferably, the first sheath portion 71 has an inner diameter 90 which closely approximates the outer diameter of the metallic member 80 enabling the first and second sheaths to be removable from the first and second probes. The cooperation of the hemispherical distal end 86 of the first probe 61 with the hemispherical interior surface 88 of the first sheath 71 enables light transmission from the proximal end 64 of the first probe to the distal end 76 of the second sheath through the hemispherical interface while simultaneously establishing the mechanical position of the sheath 71 on the probe 61 during insertion into the patient. The light emitted from the distal end 76 of the sheath portion 71 is at least hemispherical under this construction. A shoulder 91 on the light conducting means 82 cooperates with the termination 92 of the metallic member 80 to provide mechanical stability between the light conducting means and the metallic member as well as providing a smooth hemispherical surface at the distal end 66 of the probes 61 and 62. However, the fiber optic means may be formed flush with the shoulder 91 (not shown) of the light conducting means depending on the intended use of the device.

FIG. 7 is a magnified view of a portion of FIG. 2 illustrating the interconnection of the first sheath 71 with the intermediate member 73. A similar interconnection exists between the second sheath portion 72 and the intermediate member 73. Preferably, the intermediate portion 73 is more supple than the first and second sheath portions 71 and 72 which enable the less supple first and second sheath portions 71 and 72 to maintain the respective position on the first and second probe 61 and 62 during insertion within the duct of the patient. The sheath portion 71 is partially severed thereby defining a proximal aperture 96 between a major region 98 of the sheath portion which is adjacent the distal end 76 and a minor region 100 adjacent the proximal end of the sheath portion 71. The intermediate portion 73 which is shown as a tubing is received within the interior diameter 90 of the sheath portion and is affixed thereto by any suitable means such as adhesives, heat bonding, sonic welding or mechanical affixing as shown in U.S. Pat. No. 4,305,395. The minor region 100 is disposed in a first position at an acute angle relative to the major region 98 for permitting entry of probe 61 into proximal aperture 96. Upon removal of the probe 61, the minor region 100 is movable into a second position substantially in alignment with the major region 98 as shown in FIG. 8 to facilitate in the introduction of the intermediate portion 73 in the lacrimal duct of the patient. This arrangement permits the use of the more supple material for the interconnecting member 73 in contrast to the less supple material for the first and second sheath portion 71 and 72 and while eliminating any difficulties in inserting the intermediate member into the duct of the patient. The interconnecting portions 73 need not have the optical characteristics of the first and second sheath portions 71 and 72 since no light transmission will pass through the intermediate portion 73.

FIGS. 9-12 illustrate a second and alternate embodiment of the invention shown in FIG. 2. In this embodiment, the first probe is shown as 60A comprises a unitary fiber optic member having a distal end 66A terminating at a hemispherical surface 86A. The hemispherical surface 86A cooperates with the hemispherical interior surface 88 of the sheath 71 as shown in FIG. 9 in a manner similar to that described in FIG. 3. FIG. 10 is a sectional view of FIG. 9 showing the relative diameter of the probe 61A and the internal diameter 90 of sheath 71. FIGS. 11 and 12 are sectional views similar to views 5 and 6 showing the first probe being a unitary fiber optic member.

FIGS. 13 and 14 illustrate the insertion of the probes 61 and 62 and accompanying sheaths 71 and 72 into the lacrimal ducts. FIG. 13 shows the first probe 61 and first sheath 71 being inserted into the superior canal 34 and extending downwardly through the nasolacrimal duct 26. The distal end 76 is illuminated in the nose cavity 28 for facilitating location by the physician. FIG. 14 illustrates the insertion of the second probe 62 and sheath 72 into the inferior canal 36 with the the distal end 76, thereof being illuminated for facilitating location of the second sheath in the nose cavity of the patient. It should be appreciated that the probes 61 and 62 and accompanying sheaths 71 and 72 are each inserted separately within the respective canaliculi. Accordingly, only a single light source required for operation with the present invention. The specific method contemplated for use with the present invention is set forth in U.S. Pat. No. 4,305,395 which is hereby incorporated by reference.

FIG. 15 illustrates a third embodiment of the invention which is useful in many medical treatments. In this embodiment, the intubation device 140 includes base means 151 which is suitable for attachment to the light source 42. The base means 151 preferably comprises a cylindrical portion 154 for removably receiving at least a portion of the light source within an end portion 155. An end wall 156 supports an end boss 157 having an end wall aperture 158. A rim 159 is disposed on the outer periphery of the base means 151 for facilitating removal of the base means from the light source 42. It should be appreciated that the base means 151 is substantially identical to the first and second bases 51 and 52 heretofore described. The light source 42 is shown in the operative position with the base means 151.

Probe means 161 which may be identical to the first and second probes 61 and 62 has a proximal end 164 and a distal end 166 with the proximal end 164 being received within the end wall aperture 158 to permit the entry of light from the bulb 44 into the proximal end 164 of the probe means 161. The probe means 161 includes light conducting means to permit the transmission of light along the interior length of the probe between the proximal end 164 and the distal end 166 as heretofore described.

A flexible translucent tubing means shown generally as 170, includes a sheath portion 171 and a trailing portion 173. The sheath portion 171 has a proximal end 174 and a closed distal end 176 in a manner similar to FIGS. 2-14. The trailing portion 173 which is preferably a more supple material than the sheath portion 171 is secured to the proximal end 174 of the sheath portion 171 in a manner described with reference to FIGS. 7 and 8. However, the sheath portion 171 and the trailing portion 174 may be a unitary member of the same material.

The trailing portion 173 includes a stop means 177 on the terminating end 179 thereof. The stop means 177 may be formed by an suitable means such as deforming the terminating end 179 of the trailing portion 174 or by securing a stop means to the terminating end 179 of the trailing portion 174.

The embodiment shown in FIG. 15 is inserted in a similar manner as set forth in FIGS. 13 and 14. With reference to FIG. 13, the probe 161 and sheath 171 is inserted into the superior canal 34 to extend downwardly through the nasolacrimal duct 26. The distal end 176 is illuminated in the nose cavity 28 for facilitating location by the physician. The probe 161 is removed from the sheath portion 171 and the distal end 176 of the sheath portion 171 is pulled by the physician until the trailing portion 174 is disposed on the lacrimal duct and the stop means 177 is located proximate the puncta lacrimalia 30. A second probe and sheath (not shown) which is identical to the probe 161 and sheath 171 is then inserted into the inferior canal 36 in a similar manner. The stop means 177 facilitates removal of the trailing portion 173 from the lacrimal duct after the treatment is completed by the physician.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed:
1. In intubation device for use with a light source for the reconstruction of the lacrimal ducts of a patient, comprising:
   first and second base means each being suitable for attachment to the light source;
   a first and a second probe each having a proximal end and a distal end with the proximal ends connected to said first and second base means, respectively, to permit the entry of light from the light source to the proximal ends of said first and second probes;
   each of said probes having a light conducting means to permit the transmission of light along the interior length of said probes between said proximal end and said distal end;

a flexible translucent tubing means including a first and second sheath portion and an intermediate portion;

each of said sheath portions having a proximal end and a closed distal end with said intermediate portion interconnecting said first and second sheath portions;

said first and second sheath portions removably encompassing said first and second probes with said distal ends of said sheath portions being adjacent said distal ends of said probes respectively;

each of said first and second probes and said first and second sheath portions being insertable into the lacrimal ducts of the patient with said distal ends of said first and second sheath portions being illuminated by the light source to aid in the location of each of said distal ends within the nasal cavity of the patient;

said first and second probes being removable from said first and second sheath portions enabling said distal end of said first and second sheath portions to be pulled into the nasal cavity of the patient to position said intermediate portion into the lacrimal duct.

2. An intubation device as set forth in claim 1, wherein each of said first and second base means comprises a cylindrical portion for removably receiving at least a portion of the light source within one end of said cylindrical portion.

3. An intubation device as set forth in claim 2, wherein each of said first and second base means includes an end wall disposed adjacent to the other end of said cylindrical portion; and each of said end walls having an end wall aperture for respectively receiving said proximal ends of said first and second probes therein.

4. An intubation device as set forth in claim 3, wherein each of said end walls includes an end boss extending from said end wall and disposed about said end wall aperture for supporting said probe.

5. An intubation device as set forth in claim 1, wherein each of said first and second base means comprises a deformable material for friction engagement with the light source.

6. An intubation device as set forth in claim 1, wherein said light conducting means comprises fiber optic means.

7. An intubation device as set forth in claim 1, wherein each of said first and second probes includes a metallic tubing having a hollow interior; and said light conduction means comprises fiber optic means disposed within said hollow interior of each of said first and second probes.

8. An intubation device as set forth in claim 1, wherein said first and second sheath portions of said flexible translucent tubing means is less supple than said intermediate portion for maintaining the position of said first and second sheath portions on said first and second probes respectively.

9. An intubation device as set forth in claim 1, wherein each of said first and second sheath portions comprise a hollow tubing having a light transmitting wall at the distal end thereof;

said intermediate portion comprising a flexible tubing; and connecting means for connecting said intermediate portion to said first and second sheath portions in proximity to said proximal ends of said first and second sheath portions.

10. An intubation device as set forth in claim 9, wherein said first and second sheath portions are partially severed defining a proximal aperture between a major region adjacent said distal end of said sheath portion and a minor region adjacent said proximal end of said sheath portion;

said connecting means comprising said intermedate portion being received within the interior of said minor region of each of said first and second sheaths; and said minor region being disposed at an angular relationship relative to said major region enabling said probe to be inserted into said proximal aperture.

11. An intubation device as set forth in claim 10, wherein said minor portion is movable to a position substantially in alignment with said major region of said sheath to facilitate the introduction of said intermediate portion into the lacrimal ducts of the patient.

12. An intudation device for use with a light source for intubating a duct of patient, comprising:

base means being suitable for attachment to the light source;

a probe having a proximal end and a distal end with the proximal end connected to said base means to permit the entry of light from the light source to the proximal end of said probe;

said probe having a light conducting means to permit the transmission of light along the interior length of said probe between said proximal end and said distal end;

a flexible translucent tubing means including a sheath portion and a trailing portion;

said sheath portion having a proximal end and a closed distal end with said trailing portion being interconnected to said sheath portion;

said sheath portion removably encompassing said probe with said distal end of said sheath portion being adjacent said distal end of said probe;

said probe and said sheath portion being insertable into the duct of the patient with said distal end of said sheath portion being illuminated by the light source to aid in the location of said distal end;

said sheath portion being partially severed for defining a proximal aperture between a major region adjacent said distal end of said sheath portion and a minor region adjacent said proximal end of said sheath portion;

said connecting means comprising said trailing portion being received within the interior of said minor region of said sheath portion;

said minor region being disposed at an angular relationship to said major region enabling said probe to be inserted into said proximal aperture; and said probe being removable from said sheath portion enabling said distal end of said sheath portion to be pulled to position said trailing portion into the duct of the patient.

13. An intubation device as set forth in claim 12, wherein said sheath portion of said flexible translucent tubing means is less supple than said trailing portion for maintaining the position of said sheath portion on said probe.

14. An intubation device as set forth in claim 12, wherein said sheath portion comprise a hollow tubing having a light transmitting wall at the distal end thereof;

said trailing portion comprising a flexible tubing; and connecting means for connecting said trailing portion to said sheath portion in proximity to said proximal end of said sheath portion.

15. An intubation device as set forth in claim 12, wherein said minor portion is movable to a position substantially in alignment with said major region of said sheath portion to facilitate the introduction of said portion into the duct of the patient.

16. An intubation device as set forth in claim 12, including stop means disposed at the terminating end of said trailing portion.

17. An intubation device as set forth in claim 16, wherein said stop means is larger in size than the diameter of said trailing portion.

18. An intubation device for use with a light source for the reconstruction of the the lacrimal ducts of a patient, comprising:

first and second base means;

each of said base means comprising a cylindrical portion for removably receiving at least a portion of the light source within one end of said cylindrical portion;

each of said first and second base means including an end wall disposed adjacent to the other end of said cylindrical portion with each of said end walls having an end wall aperture;

a first and a second probe each having a proximal end and a distal end with the proximal ends being received within said end wall apertures of said first and second base means, respectively;

each of said probes having a light conducting means to permit the transmission of light along the interior length of said probe between said proximal end and said distal end;

each of said first and second probes including a metallic tubing having a hollow interior;

said light conduction means comprising fiber optic means disposed with said hollow interior of each of said first and second probes;

a flexible translucent tubing means including a first and second sheath portion and an intermediate portion;

each of said sheath portion having a proximal end and a closed distal end with said intermediate portion being interconnected said first and second sheath portions;

said first and second sheath portions removably encompassing said first and second probes with the distal ends of said sheath portions being adjacent said distal ends of said probe, respectively;

each of said first and second probes and said first and second sheaths being insertable into the lacrimal ducts of the patient with said distal end of said first and second sheath portion being illuminated by the light source to aid in the location of said distal ends within the nasal cavity of the patient; and said first and second probes being removable from said first and second sheath portions while said sheath portions are disposed in the lacrimal duct enabling said distal end of said first and second sheath portions to be pulled into the nasal cavity of the patient to position said trailing portion into the lacrimal duct.

19. A method of intubating lacrimal ducts of a patient comprising:

providing an intubation device including:

a light source;

a first and second base means each being suitable for attachment to said light source;

a first and a second probe each having a proximal end and a distal end with the proximal ends connected to said first and second base means, respectively;

each of said probes having a light conducting means to permit the transmission of light along the interior length of said probes between said proximal end and said distal end;

a flexible translucent tubing means including a first and second sheath portion and an intermediate portion;

each of said sheath portions having a proximal end and a closed distal end with said intermediate portion interconnecting said first and second sheath portions;

said first and second sheath portions removably encompassing said first and second probes with the distal ends of said sheath portions being adjacent said distal ends of said probes respectively;

conducting an intubation procedure comprising:

introducing said first and second sheath portions encompassing said first and second probes through the puncti lacrimalia, the canaliculi, the lacrimal sac, the nasolacrimal ducts and into the nasal cavity;

illuminating said the light source to enable illumination of said distal ends of said first and second sheath portions;

grasping said illuminated distal ends of said first and second sheath portions;

withdrawing said first and second probes from said first and second sheath portions;

pulling said sheath portions through the nasal cavity;

positioning said intermediate portion of said flexible translucent tubing means within the lacrimal ducts; and separating said intermediate portion from said first and second sheath portions.

* * * * *